(12) United States Patent
Buhlmann et al.

(10) Patent No.: US 8,565,888 B2
(45) Date of Patent: *Oct. 22, 2013

(54) AUTOMATED ADAPTIVE MUSCLE STIMULATION METHOD AND APPARATUS

(75) Inventors: Felix Buhlmann, Lausanne (CH); Pierre-Yves Lampo, Morrens (CH); Pierre Rigaux, Verlaine (BE); Pierre-Yves Mueller, Collonge-Bellerive (CH); David Truffer, Ecublens (CH); Klaus Schonenberger, Vufflens-la-Ville (CH)

(73) Assignee: Compex Medical S.A., Ecublens (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/354,736

(22) Filed: Jan. 20, 2012

(65) Prior Publication Data

US 2012/0116478 A1 May 10, 2012

Related U.S. Application Data

(63) Continuation of application No. 12/321,691, filed on Jan. 23, 2009, which is a continuation of application No. 11/046,524, filed on Jan. 28, 2005, now Pat. No. 7,499,746.

(60) Provisional application No. 60/540,871, filed on Jan. 30, 2004.

(51) Int. Cl.
  *A61N 1/36* (2006.01)
(52) U.S. Cl.
  USPC .......................................................... 607/48
(58) Field of Classification Search
  USPC .................. 607/1, 2, 46, 48, 49, 62
  See application file for complete search history.

(56) References Cited

U.S. PATENT DOCUMENTS

| 3,628,538 A | 12/1971 | Vincent et al. |
| 3,810,457 A | 5/1974 | Bottcher et al. |

(Continued)

FOREIGN PATENT DOCUMENTS

| JP | 2004129699 A | 4/2004 |
| WO | WO-2004/084988 | 10/2004 |

OTHER PUBLICATIONS

Scott Mclean, *MMG Summary*, Biomechanics and Movement Science, Mar. 30, 1998, website—http://isb.ri.ccf.org/biomch-l/archives/biomch-1-1998-03/00211.html.

(Continued)

*Primary Examiner* — Carl H Layno
*Assistant Examiner* — Jon Eric C Morales
(74) *Attorney, Agent, or Firm* — Ropes & Gray LLP (57) ABSTRACT

An automated adaptive muscle stimulation system and method are disclosed. The stimulation system includes at least one electrode assembly adapted to deliver a muscle stimulation signal to the tissue of a user, a sensor system adapted to detect a muscle response, and an electrical stimulation device operably coupled to the at least on electrode assembly and the sensor system, the electrical stimulation device including a control system operable to automatically diagnose at least one characteristic of a muscle from the detected muscle response and adjust at least one parameter of the muscle stimulation signal in response thereto to deliver an adjusted muscle stimulation signal. A dual mode muscle stimulation system adapted to accept first and second data sets and provide first and second levels of treatment data is also disclosed.

20 Claims, 10 Drawing Sheets

(56) References Cited

U.S. PATENT DOCUMENTS

| | | | |
|---|---|---|---|
| 4,167,189 A | 9/1979 | Tachi et al. | |
| 4,363,324 A | 12/1982 | Kusserow et al. | |
| 4,372,319 A | 2/1983 | Ichinomiya et al. | |
| 4,769,881 A | 9/1988 | Pedigo et al. | |
| 4,785,813 A | 11/1988 | Petrofsky | |
| 4,805,636 A | 2/1989 | Barry et al. | |
| 4,811,742 A | 3/1989 | Hassel et al. | |
| 4,817,628 A | 4/1989 | Zealear et al. | |
| 4,838,272 A | 6/1989 | Lieber | |
| 4,969,460 A | 11/1990 | Callaghan et al. | |
| 5,070,873 A | 12/1991 | Graupe et al. | |
| 5,117,840 A | 6/1992 | Brenman et al. | |
| 5,123,425 A | 6/1992 | Shannon, Jr. et al. | |
| 5,131,401 A | 7/1992 | Westenskow et al. | |
| 5,183,040 A | 2/1993 | Nappholz et al. | |
| 5,184,617 A | 2/1993 | Harris et al. | |
| 5,263,489 A | 11/1993 | Johnson et al. | |
| 5,350,414 A | 9/1994 | Kolen | |
| 5,474,574 A | 12/1995 | Payne et al. | |
| 5,507,788 A * | 4/1996 | Lieber | 607/48 |
| 5,549,656 A | 8/1996 | Reiss | |
| 5,571,144 A | 11/1996 | Schroeppel | |
| 5,775,331 A | 7/1998 | Raymond et al. | |
| 6,129,744 A | 10/2000 | Boute et al. | |
| 6,132,387 A | 10/2000 | Gozani et al. | |
| 6,233,472 B1 | 5/2001 | Bennett et al. | |
| 6,256,557 B1 | 7/2001 | Avila et al. | |
| 6,282,448 B1 | 8/2001 | Katz et al. | |
| 6,324,432 B1 | 11/2001 | Rigaux et al. | |
| 6,498,950 B1 | 12/2002 | Bradley | |
| 6,658,301 B2 | 12/2003 | Loeb et al. | |
| 7,499,746 B2 * | 3/2009 | Buhlmann et al. | 607/2 |
| 2001/0031916 A1 | 10/2001 | Bennett et al. | |
| 2002/0161409 A1 | 10/2002 | Rouw et al. | |
| 2002/0161415 A1 | 10/2002 | Cohen et al. | |
| 2002/0165590 A1 | 11/2002 | Crowe et al. | |
| 2003/0074037 A1 | 4/2003 | Moore et al. | |
| 2003/0083711 A1 | 5/2003 | Yonce et al. | |
| 2003/0100932 A1 | 5/2003 | Ciaff | |
| 2003/0195586 A1 | 10/2003 | Rigaux et al. | |
| 2003/0195587 A1 | 10/2003 | Rigaux et al. | |
| 2003/0208246 A1 | 11/2003 | Kotlik et al. | |
| 2005/0137629 A1 | 6/2005 | Dyjach et al. | |

OTHER PUBLICATIONS

Tarata, M. et al. The Accelerometer MMG Measurement Approach in Monitoring the Muscular Fatigue, Measurement Science Review. 1:1, 47-50 (2001).

Tarata, Mihai T, Mechanomyography versus Electromyography, in monitoring the Muscular Fatigue,, BioMedical Engineering Online, Feb. 11, 2003, pp. 1-10.

* cited by examiner

SHOWING 2 OF 4 CHANNELS

AUTOMATED ADAPTIVE MUSCLE STIMULATION METHOD AND APPARATUS

CROSS-REFERENCE TO RELATED APPLICATION

This application is a continuation of U.S. patent application Ser. No. 12/321,691 filed on Jan. 23, 2009, which is a continuation of U.S. patent application Ser. No. 11/046,524 filed on Jan. 28, 2005, now U.S. Pat. No. 7,499,746 which claims the benefit of U.S. Provisional Application No. 60/540,871 filed on Jan. 30, 2004, the entire contents of which are incorporated herein by reference.

FIELD OF THE INVENTION

The present invention relates generally to electro-stimulation. More particularly, the present invention is directed to an apparatus and method for automated adaptive muscle stimulation wherein the muscle stimulation may be adjusted by a measured muscle reaction.

BACKGROUND OF THE INVENTION

It is common practice for therapists, physicians, athletes, and other individuals to utilize various treatment and therapy devices to promote muscle training, conditioning, and growth. In addition, devices often referred to as Transcutaneous Nerve Stimulation ("TENS") units are employed to manage pain and discomfort through blocking of the nerve signal from the area of discomfort to the brain. With muscle stimulation and nerve stimulation, a device is programmed to output various levels of electrical pulses. The frequency, duration, pulse width, and intensity of the output signal control the directed treatment goals.

With regard to muscle stimulation, there are a myriad of uses for these electro-stimulation devices. Treatment categories can generally be divided between muscle fitness, muscle aesthetic, sport training, pain management, muscle rehabilitation, and vascular therapy. Each category is directed to a different stimulation goal. With muscle fitness, the goal is generally to restore, improve, or maintain a good physical condition by building muscle, muscle tone, volume, trophism, metabolism, and the like. With muscle aesthetic goals, the stimulator is often utilized on muscles in order to shape, firm, refine, increase elasticity, and increase caloric expenditure. Sports-minded individuals may use the device to increase muscular endurance and strength, increase blood flow to promote active recovery, and the like. When focus is on muscle rehabilitation, muscular stimulation is needed to restore or otherwise redevelop a convalescent muscle. Under the vascular category of treatment programs, the goal is to improve blood circulation in the stimulated area to minimize circulatory problems, fatigue, lack of oxygenation, swelling, and other related problems. In pain management applications, electro-stimulation devices are used primarily to alleviate muscle pain or other discomfort.

Regardless of the unique goal-dependent outputs of the device, electro-stimulation works under a principle of voluntary muscle contraction. When individuals contract a muscle, the brain sends the information to the muscle via the motor nerve. With electro-stimulation, a suitable electric current acts directly on the nerve by means of electrical impulses that reproduce the natural physiological phenomenon. These electrical impulses are applied to the user through attached electrodes. The electrodes are typically adhesively attached to the person or person's clothing. With electro-stimulation a patient or user can achieve intensive muscular work without mental or cardiac fatigue, thus reducing joint and tendon constraints. U.S. Pat. No. 6,324,432, commonly assigned with the present application to Compex SA, discloses an electrical neuromuscular stimulator for measuring muscle responses to electrical stimulation pulses, and U.S. Patent Application Publication No. 2003/0074037 discloses an electrical nerve stimulation device. U.S. Pat. No. 6,324,432 and U.S. Patent Application Publication No. 2003/0074037 are incorporated by reference herein in their entireties.

However, conventional electro-stimulation devices, while useful in achieving intensive muscular work for a target or generalized muscle set, are not capable of self-adjusting for various muscle groups. Conventional devices are also not capable of automatically adjusting for various users; even though two patients may be seeking the same general therapeutic or training effects, each may be at a different fitness or recovery stage. Further, conventional electro-stimulation devices are not generally able to self-adjust for detected physiological traits of a particular user.

Conventional devices also frequently require application and supervision by a trained medical professional to prevent muscle over-stimulation, fatigue, or, in extreme situations, injury. Additionally, electro-stimulation treatment delivered by conventional devices is typically less efficient because theses devices are unable to consider or account for muscle feedback. As a muscle is stimulated, it may react or respond in a manner for which adjustment of the stimulation is appropriate. For example, a fatigue level experienced by a muscle varies and generally accelerates as treatment progresses. Fatigue levels experienced and the acceleration of fatigue will be different for each user and each target muscle or group and must be carefully monitored to increase the efficiency of electro-stimulation in sports applications.

Monitoring muscle response and feedback directly is difficult and impractical in most treatment situations as such monitoring is most effectively accomplished by subcutaneous sensors. While transcutaneous applications of accelerometers or other devices are known, electro-stimulation devices presently available cannot accurately and actively self-adjust a treatment session based on detected feedback. Further, the measurements are often inaccurate because of interference from other active but non-target muscles.

U.S. Pat. No. 4,817,628 discloses a system and method for evaluating neurological function controlling muscular movements. The system generally includes an accelerometer sensor, a stimulus electrode assembly, and a portable device to which the sensor and electrode assembly are connected. The sensor measures the magnitude of the (stimulus evoked) movement of a body part of the subject along at least one axis of three-dimensional space.

U.S. Pat. No. 6,282,448 discloses a self-applied and self-adjusting device and method for prevention of deep vein thrombosis with movement detection. An accelerometer can detect motion and keep the device operating until motion is generated and/or turn the device off when motion is detected, generated by the device or user.

U.S. Patent Application Publication No. 2002/0165590 discloses an apparatus for stimulating a muscle of a subject. An accelerometer may be employed that is positioned adjacent a muscle of the subject that is being stimulated. This meter then tracks the magnitude of the shivers generated in the muscle. If this magnitude exceeds a predetermined level, the apparatus is notified and may be adjusted or shut off.

Additionally, Tarata et al. discuss general approaches used to monitor muscle fatigue in "The Accelerometer MMG Measurement Approach, in Monitoring the Muscular Fatigue,"

from the MEASUREMENT SCIENCE REVIEW, Vol. 1, No. 1, 2001, and in "Mechanomyography versus Electromyography, in monitoring the muscular fatigue," from BIOMEDICAL ENGINEERING ONLINE, published Feb. 11, 2003. McLean provides a mechanomyography summary in a subject message "MMG summary" posted to a Biomechanics and Movement Science listserver on Mar. 30, 1998. The above articles are incorporated by reference herein in their entireties.

The need remains, however, for an electrical muscle stimulation device and corresponding electrode system that substantially addresses the innate drawbacks of conventional devices and systems.

SUMMARY OF THE INVENTION

The present invention solves many of the above described deficiencies and drawbacks inherent to conventional electro-stimulation devices and treatments. In particular, the invention provides for intelligent muscle stimulation by an automated adaptive muscle stimulation system capable of adjusting stimulation parameters to user physiology, thereby enhancing user comfort, and improving treatment efficiency. This intelligent muscle stimulation system is non-invasive and can be used in tandem with other exercise or activity, thereby facilitating the integration of electrotherapy into a wider variety of treatment protocols. During use of the muscle stimulation system, the stimulation energy may be continuously monitored, verified, and adjusted. The system prevents the onset of detrimental muscle contractions and customizes treatment based upon muscle feedback and user physiology. Muscle fatigue, for example, can be one focus of the muscle feedback.

An automated adaptive muscle stimulation system in accordance with one embodiment of the invention includes at least one electrode assembly, a sensor system, and an electrical stimulation device. The electrical stimulation device includes a control system operable to automatically diagnose at least one characteristic of a muscle from a detected muscle response and adjust at least one parameter of the muscle stimulation signal in response thereto to deliver an adjusted muscle stimulation signal. The electrode assembly is operably coupled to the electrical stimulation device and is adapted to deliver a muscle stimulation signal to the tissue of a user. In one embodiment, the electrode assembly is adapted to be placed on or around a designated or predetermined body part or muscle to bring the electrode into contact with a user's skin or the clothing proximate a user's skin to deliver electrical stimulation signals via the stimulation system and detect muscle reactions and responses via the sensor system.

The above summary of the invention is not intended to describe each illustrated embodiment or every implementation of the invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

The adaptive muscle stimulation system and method of the invention provide intelligent muscle stimulation, wherein the stimulation can be adjusted by a detected muscle response, and wherein the stimulator can be used by non-medical personnel. The invention can be more readily understood by reference to FIGS. 1-10 and the following description. While the invention is not necessarily limited to such an application, the invention will be better appreciated using a discussion of exemplary embodiments in specific contexts.

Herein throughout, the term "user" will be used to refer generally to patients or persons receiving electro-therapy and electrostimulation treatments. The term "operator" will be used to refer generally to doctors, nurses, therapists, and other medical professionals, as well supervisory personnel and those having specialized or particular training relating to the use of electro-therapy devices.

Figure 1:
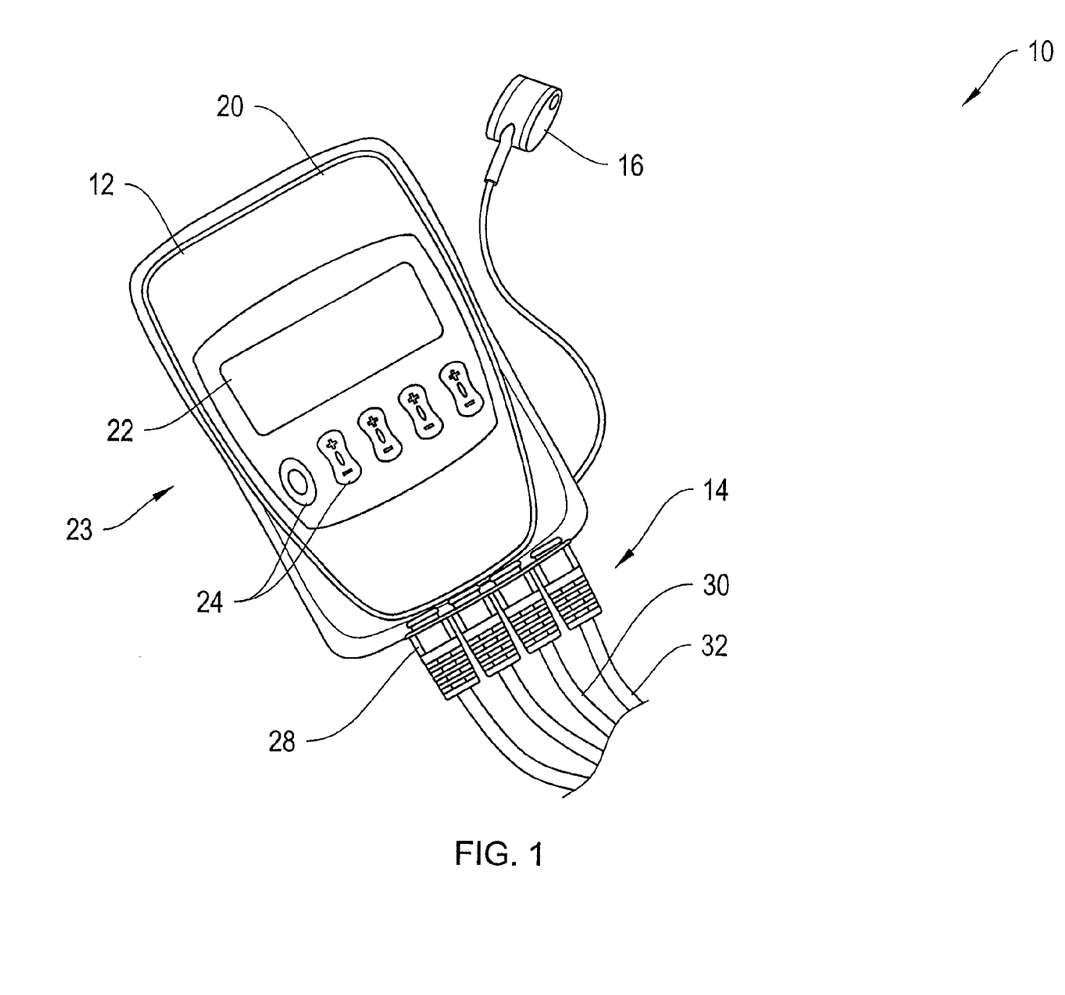
FIG. 1 is a top view of an electrical stimulation device in accordance with one embodiment of the invention.
Figure 2:
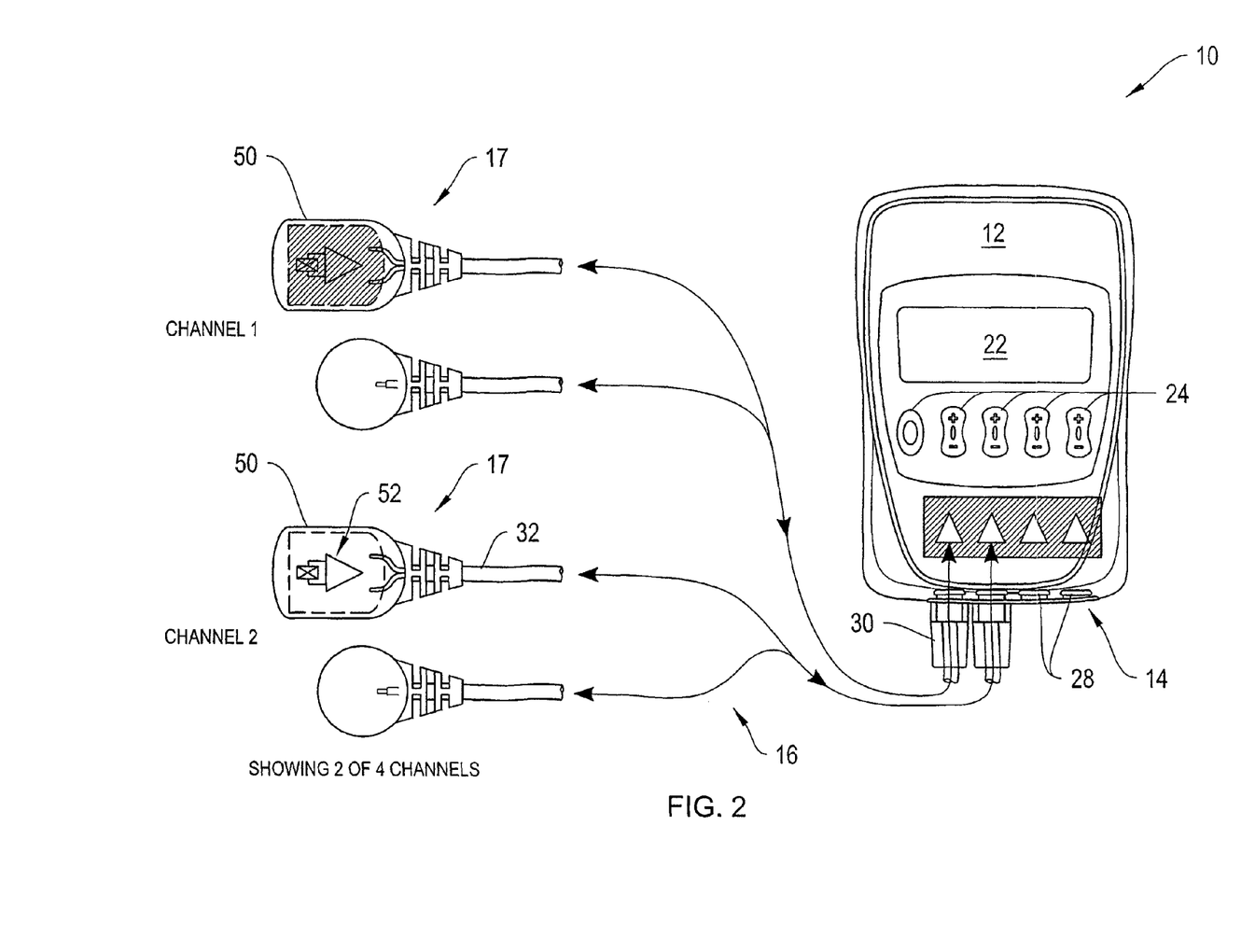
FIG. 2 is a schematic block diagram of an electrical stimulation device in accordance with one embodiment of the invention.

Referring to FIGS. 1 and 2, a muscle stimulation system 10 according to one embodiment of the invention includes an electrical stimulation device 12, an electrode interface 14, and at least one electrode assembly 16. Electrode assembly 16 can include a muscle intelligence (MI) sensor system 17 or a plurality of MI sensor systems 17. MI sensor system 17 includes a sensor device, for example an accelerometer, for detecting a muscle reaction or response to an applied electro-stimulation signal. Sensor system 17 will be described in more detail below.

In one embodiment, electrical stimulation device 12 comprises a unit housing 20; a user interface system having an input portion 24 and an output portion 23; a control system 40 (refer also to FIG. 3); and a plurality of output channels 28. Input portion 24 includes a plurality of keys or buttons in communication with control system 40 to provide menu support and selection options prior to, during, and after running of the stimulation routines. Output portion 23 includes a visual display portion 22 and, in one embodiment, an auditory output portion, for example a small external or enclosed speaker or the like (not shown).

Figure 3:
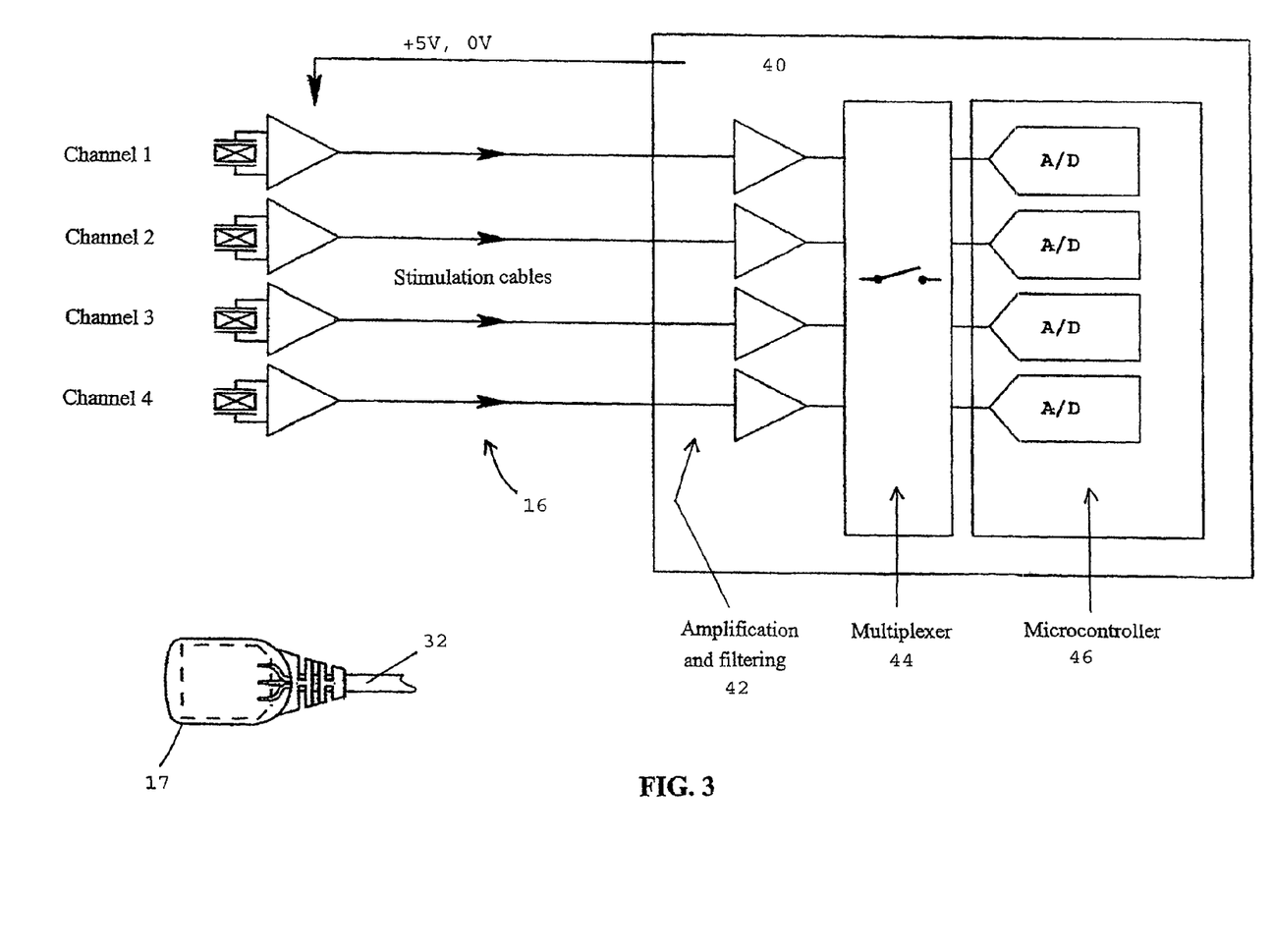
FIG. 3 is block diagram of an electrical stimulation device in accordance with one embodiment of the invention.

Referring to FIG. 3, one embodiment of control system 40 comprises a signal conditioning portion 42 effecting signal amplification and filtration, a multiplexer portion 44, and a microcontroller 46. Control system 40 is preferably programmable such that a treatment or stimulation program created, designated, or prescribed by an operator can be stored in microcontroller 46 and subsequently selected by the user to initiate a stimulation routine based upon individual needs and characteristics inputted via input portion 24. Control system 40 can be equipped with pre-programmed stimulation routines, or the routines can be selectively programmed based upon the device assignment to a particular user and according to his or her individual needs. Access to control system 40 can also be password protected or otherwise programmed to provide a first level of access to users for input of a first set of user-specified information and data and select stimulation programs and characteristics from those available via input portion 24 and output portion 23, and a second level of access providing programming capabilities, maximum and minimum stimulation parameter selection, and other operations reserved for operators such as trainers, doctors, nurses, therapists, and other medical professionals, also via input portion 24 and output portion 23.

Control system 40 is operable to control generation of electrical stimulation signals, or pulses, and subsequent delivery of the stimulation signals to a user by at least one electrode assembly 16. Based upon the desired stimulation treatment program and goals for the user as input by the user and programmed by the operator, control system 40 automatically controls and maintains the appropriate stimulation program(s) and signal characteristics.

Electrode interface 14 provides connectivity between control system 40 and electrode assembly 16 via output channels 28. In one embodiment, each electrode assembly 16 includes a connector 30 adapted to couple electrode assembly 16 to an output channel 28 at interface 14 and a cable 32. Cable 32 provides limited local separation of device 12 and electrode 16, permitting user movement during treatment and convenient storage of device 12 during use, for example in a pocket or on a belt clip or the like.

Each electrode assembly 16 includes at least one electrode 17 adapted for application to a user's tissue. In one embodiment, electrode 17 is a flexible structure having an adhesive on at least one side adapted for direct contact with a user's skin for application of stimulation signals to a user's tissue. In another embodiment, electrode 17 is a flexible structure mounted on a belt or band for application of stimulation signals to a user's tissue directly or through the user's clothing. Electrodes 17 can be applied to almost any targeted nerves, muscles, or muscle groups. For instance, electrode assembly 16 can provide electrical stimulation to the following muscles or muscle regions: stomach; abdominals; quads; calves; certain chest, thoracic, and shoulder muscles; cervical region; lumbar region; buttocks; biceps; feet; and thighs. Other regions and muscles can be targeted due to the flexible configuration options of electrodes 16 without deviating from the spirit and scope of the invention, while other regions should presently be avoided, including the cardiac and proximate regions, because of the risk of inducing cardiac fibrillation.

The invention further comprises a muscle intelligence (MI) system that makes it possible to diagnose, transcribe, and automatically adapt certain stimulation parameters to suit a particular user's physiology and muscle reactions. The MI system permits users to safely customize and adjust a muscle stimulation treatment or workout session to their individual needs, physiological characteristics, and muscle reactions, instead of being restricted to general factory pre-set default parameters. The MI sensor also provides measurement and analysis of certain physiological characteristics of the muscle in order to adapt the related stimulation parameters accordingly. The MI system is enabled primarily via an MI sensor system, or a plurality of MI sensor systems, in communication with electrical stimulation device 12 and control system 40. In one embodiment, the MI sensor system is incorporated into at least one electrode assembly 16 and forms an interactive link between the muscles being treated and stimulator 12.

Referring to FIG. 2, at least one MI sensor 50 is coupled to an output channel 28 of stimulator 12 at interface 14, replacing any one of the standard, non-MI electrodes. In one embodiment, a plurality of MI sensors 50 can be used. An electrode assembly 16 incorporating MI sensor 50 thereby includes a sensor system and a stimulation system and serves a dual function, operating as both a sensor that diagnoses the muscle and a standard electrode that provides stimulation, whether one MI sensor 50 or a plurality of MI sensors 50 are used in a particular treatment session.

In one embodiment, sensor system 50 comprises an accelerometer device 52 operable to measure and monitor muscle reaction during a treatment session. More specifically, accelerometer device 52 is operable to detect an onset, a modification, or a disappearance of a muscle response in reaction to a stimulation signal applied to the muscle by stimulation device 12. In other representative embodiments, sensor system 50 can comprise a tension strain gauge, a measurement detector, or another sensor device known to those skilled in the art.

In use, after a stimulation signal is delivered to a muscle by MI sensor 50, one of several things will occur. First, if the stimulation signal is too small, i.e., the current is too low, to stimulate the muscle to contract, the muscle will not react and no response will be detected by accelerometer device 52. Second, if the stimulation signal is high enough to stimulate the muscle, the muscle will react to some degree and a mechanical response will be detected by accelerometer device 52. Third, if the muscle is already contracted when a stimulation signal is applied, the muscle may still react at some level detectable by accelerometer device 52, or the muscle will not react because it has peaked, in which case accelerometer device 52 will detect no reaction or will detect a disappearance of a muscle reaction. In any of these situations, if the muscle reacts with either a slight twitch or a greater degree of contraction, accelerometer device 52 is operable to detect the mechanical response very quickly in the form of a reaction pulse.

In one embodiment, accelerometer device 52 detects a series of reaction pulses in response to a succession of electrical pulse signals delivered to the muscle by stimulation device 12 and communicates the detected pulses to control system 40. Control system 40 records the shapes of the series of reaction pulses detected and calculates a coefficient of correlation of the reaction pulses. This process is then repeated for subsequent pulse and reaction sequences and the series of calculated coefficients of correlation is compared.

For example, a series of stimulation pulses is applied to a particular muscle via electrode(s) 16 and subsequent muscle reactions are detected by accelerometer device 52 included within at least one electrode 16. The correlation coefficient between each of the muscle reaction signals is stored by control system 40 and compared with the other response signals. The amplitude of the correlation coefficients is recorded and changes in one coefficient from another coefficient enable control system 40 to detect either an apparition of a muscle response to the electrical pulses or a modification of the muscle state, for example a contraction of the muscle. The correlation coefficients can also be computed using an algorithm during the program duration to obtain other information about the particular muscle state.

Figure 4:
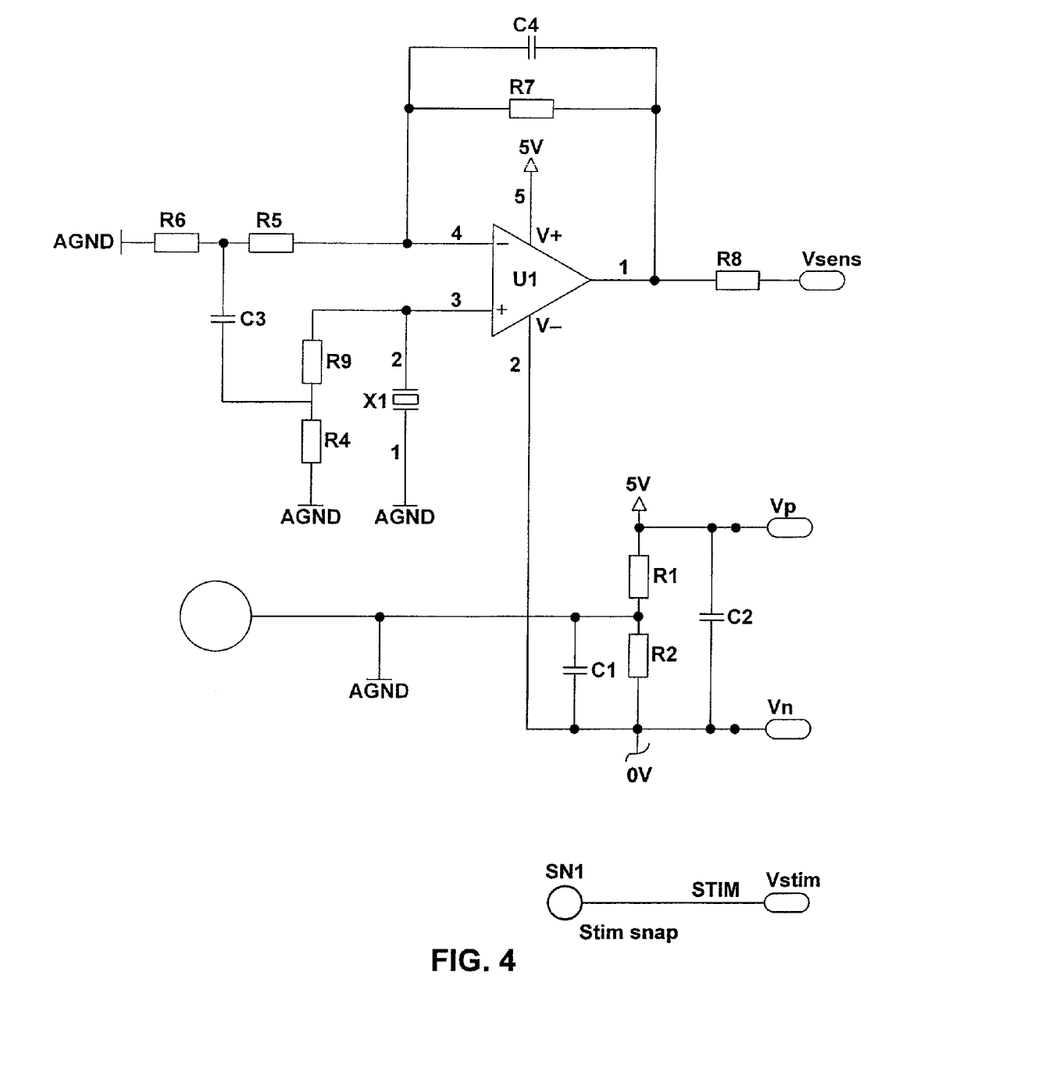
FIG. 4 is a schematic of an accelerometer circuit in accordance with one embodiment of the electrical stimulation device of the invention.

Accelerometer device 52, or a plurality of accelerometer devices 52, can be utilized in the manner described herein in cooperation with a plurality of treatment modes to customize device 12 for any user's unique physiology, target muscle or muscles, and treatment goals. The customization can be based solely upon information provided by a user, information programmed or provided by an operator, or preferably upon information from both a user and an operator. An exemplary circuit schematic in accordance with one embodiment of accelerometer device 52 of the invention is shown in FIG. 4.

Exemplary stimulator treatment modes and applications that can implemented by system 10 in cooperation with electrode 17, MI sensor 50, and accelerometer device 52 are described in further detail below.

MI-Scan

The muscle intelligence scan (MI-scan) function adapts an electrical muscle stimulation session to the physiology of a particular user. Just prior to beginning a stimulation session, system 10, via control system 40, electrode assembly 16, and sensor system 50, scans and measures the excitability of the target muscle group and automatically adjusts the relevant stimulator parameters to the excitability of the target muscle group. The resulting measurement is user-customized. The MI-scan function is accessible by all programs involving a muscular contraction, and therefore also requiring electrical stimulation pulse width adjustment, of the target muscle or muscles, particularly those programs requiring the choice of a muscle group.

Figure 5:
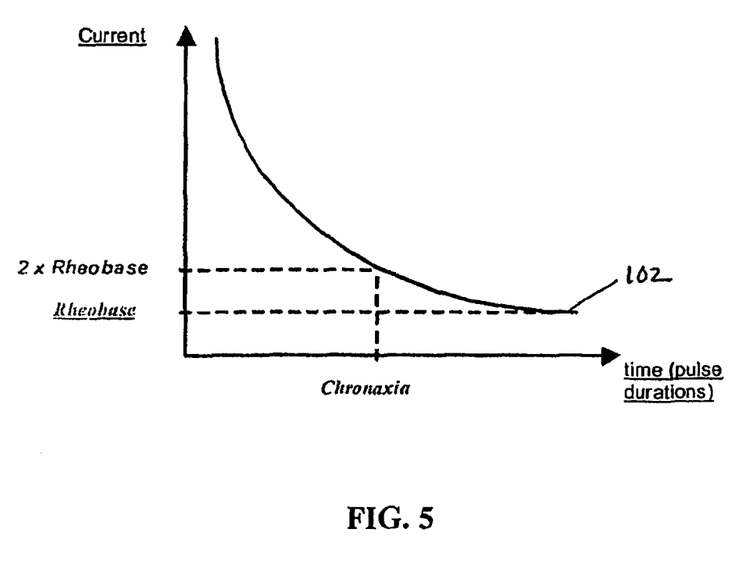
FIG. 5 is an exemplary graph depicting a chronaxia point in accordance with one embodiment of the invention.

The MI-scan function allows a user to adapt the characteristics of the stimulation signals and pulses to the individual specificities of each user and the excitability characteristics of the stimulated muscle, i.e., a muscle chronaxia. Referring to FIG. 5, the rheobase, Rh, is the minimum intensity necessary to stimulate a muscle with an infinite impulse duration:

$$Rh=i$$

Muscle chronaxia is a characteristic applied pulse duration required to achieve optimum stimulation of a particular muscle at an intensity that is twice the rheobase, or 2 Rh. Muscle chronaxia is dependent upon the particular muscle group and subject, according to Lapicque's Law:

$$I = \frac{q}{t} + i,$$

wherein I is the intensity of a stimulation current; q is an experimentally determined coefficient that corresponds to a certain quantity of electrical charges; t is an impulse duration; and i is a current intensity. A conventional muscle stimulator uses rectangular impulses with a fixed pulse width. Therefore, in these systems, the current output is adjusted through the intensity. For instance, a rectangular impulse of 200 microseconds (µS) would have a pulse width with an adjustable intensity setting between 0 and 100 mAmp.

According to principles of electro-physiology, the optimal pulse width is equal to or approximates the chronaxia of the target motorneurons, which results in more comfort and a more specific excitement of the target motorneurons. Because the pulse width may vary from a first target muscle to another target muscle, using the intensity as a scale of current output is not reliable. Nevertheless, as conventional muscle stimulators are not equipped with a chronaxia measurement system, these stimulators must use a fixed pulse width that is not optimum.

Control system 40, in communication with the sensor system 50 and accelerometer device 52, determines a muscle chronaxia during a measurement phase of about one to several seconds. This measurement phase comprises applying several different pulse durations to the target muscle in order to determine points of the curve depicted in FIG. 5. By mathematical curve fitting, the value of chronaxia can be determined. This function is preferably implemented at the start of the program by a short sequence during which measurements are taken. Once the test has been completed, the primary stimulation program can start.

Referring to FIG. 5 in conjunction with FIGS. 1-3, MI sensor system 50 in cooperation with device 12 and control system 40 is able to measure, through a short initial test, the chronaxia of the motorneurons of the target stimulated muscle. Device 12 then automatically adjusts the pulse width equal to the measured chronaxia. Above excitation curve 102 depicted in FIG. 5, a muscle reaction is initiated, which can be detected by sensor system 50. Because the intensity is not a reliable current output scale when the impulse width varies from muscle to muscle or from one session of stimulation to another, control system 40 of the invention uses an energy scale instead of an intensity scale.

Figure 6:
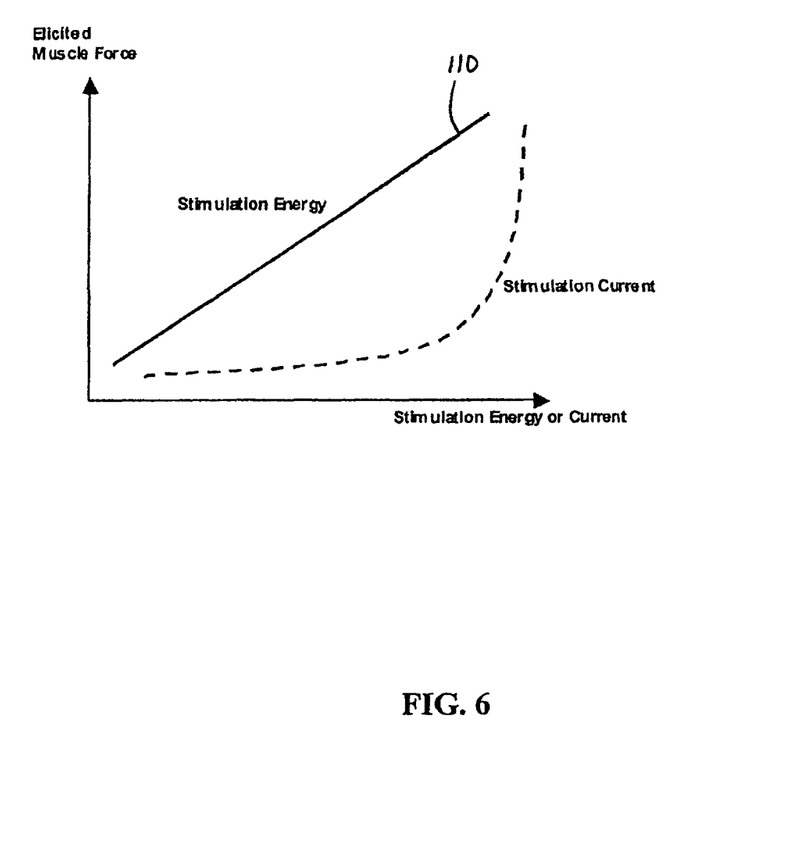
FIG. 6 is an exemplary energy measurement scale graph in accordance with one embodiment of the invention.

Referring to FIG. 6, a progression of the stimulation energy 110 is linear, producing a more comfortable stimulation as realized by a user. Stimulation energy 110 can be expressed as E according to the following equation in one embodiment:

$$E=RI^2t,$$

in which R is a resistance of target muscle tissue expressed in Ohms; I is a stimulation current expressed in milliamps; and t is a pulse duration expressed in seconds. The stimulation force, F, can then be expressed as follows:

$$F=zRI^2t,$$

wherein z is a constant. Thus:

$$F \sim E,$$

F varies linearly with E but not with I.

In operation, the energy output is adjustable by a user in terms of a percentage of the maximum energy output. This new scale of power output additionally has an advantage compared to the intensity or quantity of electrical charges. The practical advantage is that the strength of the contraction brought about by the stimulation has a linear relationship with the energy, as depicted in FIG. 6. As a result, the user has smoother and safer control of the contraction by acting through an energy scale that corresponds to a physiological response. The user, or an operator, can adjust the energy scale to a desired setting in order to achieve the desired level of contraction strength. In one embodiment, the operator defines an available energy scale and may or may not provide the user with fine adjust within that available scale. Because device 12 is a current generator, control system 40 and microcontroller 46 control the electrical intensity output adjustment according to the mathematical relationship between energy and intensity. In other words, the operator or, if permitted by the operator, the user to a predetermined degree, can set a desired energy level of stimulation and the microprocessor translates this demand as a variation of intensity.

In one embodiment, the energy scale has approximately 1000 levels, or steps, with settings running from step zero to step 999. The pulse width and the intensity are determined for each energy step, wherein each step can have slight pulse width variations during energy level variations. The maximum stimulation energy, Max E, during an electrical pulse is:

$$\text{Max } E = (\text{Max } I)^2 * R * \text{Max } W,$$

wherein Max I is the maximum current and W is the pulse width. In one embodiment of system 10, the Max I is approximately 120 milliamps (mA), Max W is approximately 400 microseconds (μs), and the resulting Max E is:

$$(120)^2 * 400 = 5,760,000 \text{ mA}^2 * \mu s.$$

If system 10 has 1000 energy steps, each step represents one thousandth of the maximum energy, Max E. In one embodiment in which system 10 has an automatic ramp, the energy variation will be linear from step to step, using as many energy levels as possible. In another embodiment, a user can self-adjust the stimulation level, wherein each increase requested by a user via input portion 24 results in a one energy level increase within a first range of step 0 to about step 99. In a second range from about step 100 to about step 999, each increase requested by a user produces an energy level increase according to the following equation:

$$\text{New Level} = \text{Old Level} + \frac{\text{Old Level}}{64}$$

Figure 7:
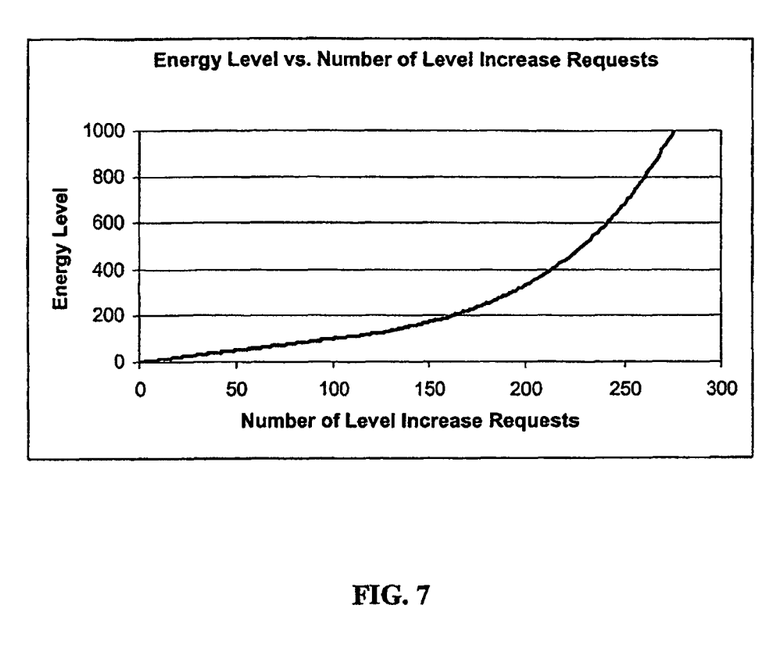
FIG. 7 is an energy graph according to one embodiment of the invention.

This results in the curve of FIG. 7.

When a desired energy level to be set is known, the current intensity can be adjusted to achieve the desired level. The corresponding current is then:

$$I = \sqrt{\frac{\text{Max } E}{W_0} \cdot \frac{\text{Energy Level}}{1000}},$$

wherein $W_0$ is an uncorrected pulse width. The variations of the intensity output preferably have about a half milliamp (mA) of minimum sensitivity adjustment. This minimum intensity adjustment is not precise enough, however, to provide an energy scale of 1000 steps. For example, if the calculated intensity for the desired energy setting according to the preceding equation is I=87.6586 mA, the real intensity output would be $I_{Corrected}$=about 87.5 mA, rounded to the nearest 0.5 mA value. Such intensity inaccuracy would be responsible for any difference between the desired energy and the real energy output.

In order to solve the problem and retain the full preciseness of the intended 1000 steps of the energy scale, microcontroller 46 calculates a pulse width correction according to the following equation:

$$W_{Corrected} = \frac{\text{Energy Level}}{1000} \cdot \frac{\text{Max } E}{I^2_{Corrected}}$$

Figure 8:
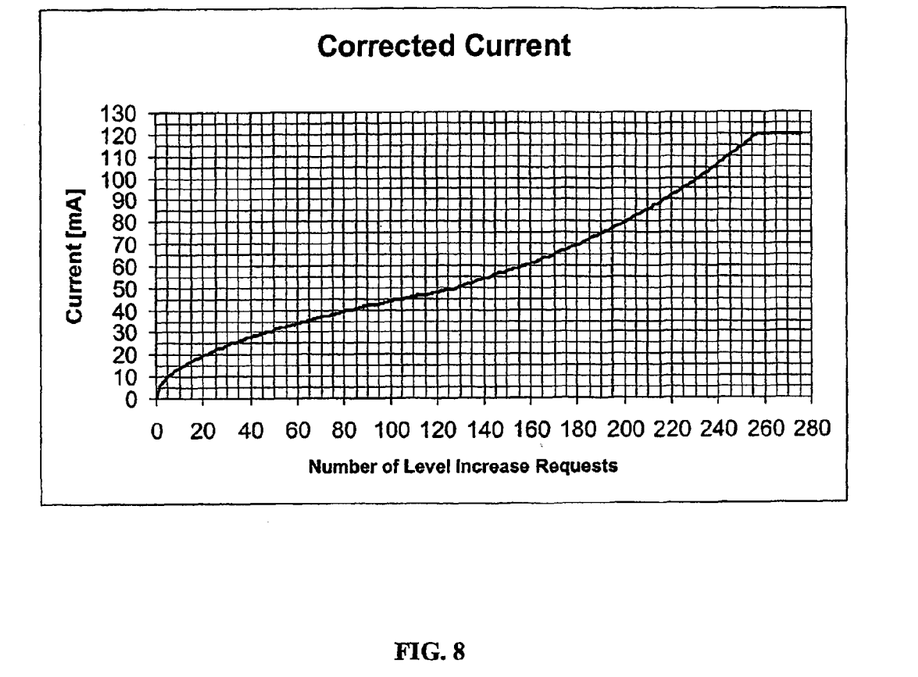
FIG. 8 is a current graph according to one embodiment of the invention.
Figure 9:
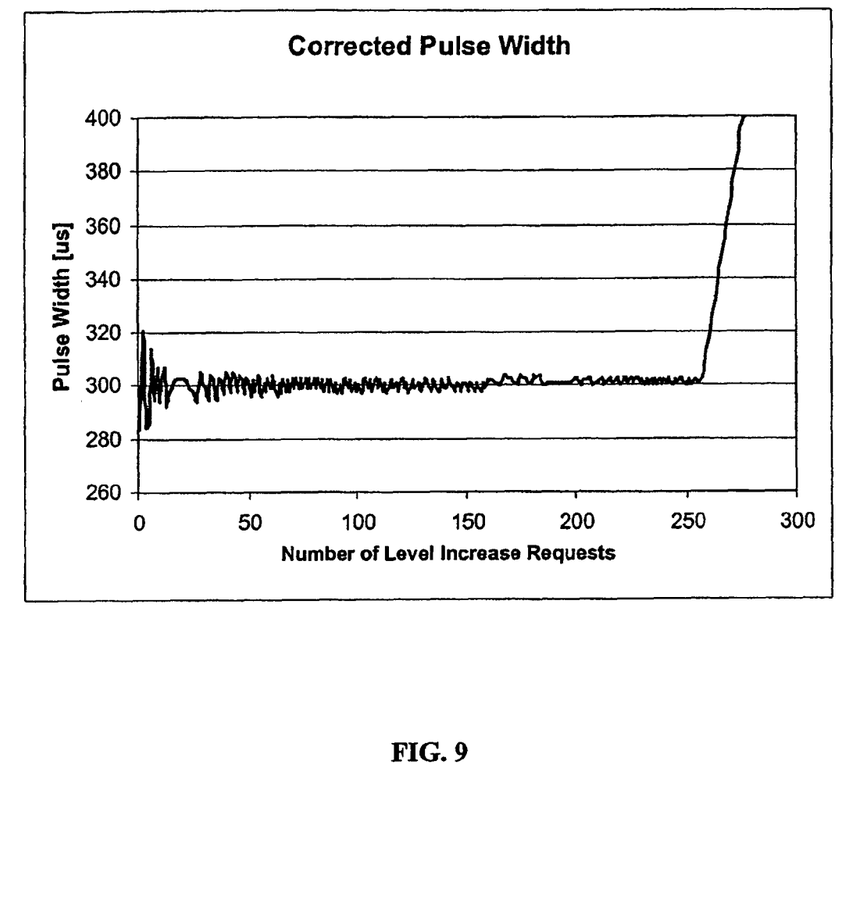
FIG. 9 is a pulse width graph according to one embodiment of the invention.

Slight pulse width adjustments therefore compensate the half by half milliamp current output adjustment in order to provide the user or operator with a more precise energy scale of 1000 steps. In general, the difference between $W_0$ and $W_{Corrected}$ will be minimal, except at very low energy levels and approaching a maximum current. By way of further example, FIG. 8 shows an evolution of current, I, and FIG. 9 shows an evolution of pulse width, W, for each step increase request, each at an uncorrected pulse width of W=300 μs.

In another exemplary embodiment, the maximum current output of device 12 is approximately 120 mA and the maximum pulse width is approximately 400 μS. If the measured chronaxia from sensor 50 is, for example, about 200 μS and the current output is at a maximum of about 120 mA, the maximum energy power of device 12 is not yet reached. In most instances, users do not need to use an energy higher than the one provided with the 120 mAmp, but some operators, particularly trainers and medical personnel working with professional athletes or other high performance users, would prefer to have access to the full device power for some specific trainings. Stimulator system 10 of the invention gives the operator or, if permitted by the operator, the user to a predetermined degree, the option of overriding the energy provided with the maximum intensity through an increase of the pulse width when it is not yet at the maximum of about 400 μS.

MI-Action

The MI-action mode is a work mode in which a voluntary muscular contraction is automatically accompanied by a contraction caused by electro-stimulation. The electro-stimulation contraction is therefore controlled and the working session becomes more comfortable (from both the psychological and muscular standpoints), more intensive (the muscle works more and in greater depth), and more complete (improvement of coordination). The MI-action mode allows the user to start the muscular contraction phase by voluntarily contracting the stimulated muscle, thereby offering an opportunity to associate voluntary work with stimulation.

In operation, accelerometer 52, as part of MI sensor system 50, senses muscle twitches that are elicited by brief electrical test pulses during the resting phases. As soon as the twitch signal is modified or altered as detected by MI sensor 50 by the voluntary contraction, device 12 sends a stimulation signal to the muscle such that a voluntary contraction and an electrical stimulation occur simultaneously. The user can thus start the electrical muscle contraction at his or her convenience by triggering its onset with a voluntary muscle contraction. Further, the simultaneous voluntary contraction and electrical stimulation improve training efficiency by increasing the number of muscle fibres that are activated.

The voluntary start of a contraction during an active rest phase is possible within a given time span that varies depending on the stimulation treatment program used. In one embodiment, an alteration of sound signals from output portion 23 delimits this time span as follows:

An initial sound signal of increasingly close alerts indicates that the start of the voluntary contraction phase is possible.
  A continuous sound signal indicates that it is the ideal time to start the voluntary contraction phase.
  A decreased sound signal indicates that start is still possible and the work rate is still satisfactory.
  After a certain time, which varies depending on the program, during which the alerts are more spaced out, the device automatically goes into the "Pause" mode if no contraction phase has been started.

The MI-action mode is thus a bridge between voluntary workout and electro-stimulation with a goal of increasing training efficiency.

MI-TENS

TENS is an analgesic stimulation technique in which only the sensory nerves are excited and not the motor nerves. During pain management treatment in MI-TENS mode, the onset of a muscle contraction is an unwanted affect that appears when intensity is raised above a particular level. In order to obtain an efficient TENS treatment, however, the intensity should be set as high as possible yet remain below the threshold of motor nerve excitation, which results in muscle contraction.

MI-TENS is a feature preventing the onset of muscle contraction automatically. On the basis of the measurements taken regularly during the session by sensor system 50, device 12 automatically readjusts the stimulation energy to avoid an onset of muscular contraction. Accelerometer 52 and MI sensor 50 sense muscle twitches that are elicited by brief electrical test pulses during the MI-TENS treatment. When a muscle contraction occurs, MI sensor 50 detects an onset of the twitch response to the test pulse. This event indicates that the muscle contraction has occurred. Accordingly, control system 40 automatically reduces the stimulation intensity, or energy, down to a level where the twitches are no longer detected, meaning that the contraction has disappeared. In other words, the MI-TENS is a supervisor that prevents the user from increasing energy to a level where counter-indicated muscle contraction occurs.

MI-Range

The MI-range function indicates the ideal energy adjustment range for the low frequency stimulation programs, for example analgesic, rehabilitative, and vascular muscle electrostimulation programs, in which muscle twitches are required to increase blood flow to a particular area. Using MI-range, a user no longer needs to question whether the energy applied is too high or too low as this function provides the necessary information, thus optimising the efficiency of treatment.

The MI-range function indicates the ideal energy adjustment range for a program whose efficiency requires vigorous muscular twitches and is therefore accessible only for stimulation treatment programs using low stimulation frequencies, generally those less than about 10 Hertz in one embodiment. In programs permitting the use of the MI-range function, stimulator device 12 checks whether a user is currently in the ideal energy range. In one embodiment, if the user is below the range, stimulator device 12 prompts the user to increase the energy by displaying "+" signs or another indicator prompt on display 22 or an audible prompt via input portion 24. Once stimulator device 12 and sensor system 50 have detected the user-ideal adjustment range by detecting at least one user physiological characteristic, a bracket or similar indicator appears adjacent the bar chart on display 22 of channel 28 to which sensor system 50 is connected. This bracket indicates the energy range within which the user should work for optimal stimulation. If the user adjusts the stimulation energy below the ideal treatment range, stimulator device 12 prompts the user to increase it again with an audio and/or visual indicator, for example a continuous display of blinking "+" signs on display 22, an audible tone, a combination of visual and audible prompts, or the like. Thus, in the MI-range function, device 12 detects the muscle twitches and recommends a range for effectiveness suited for a user's individual physiological characteristics.

Energy Level Setting Assistance

The energy level setting assistance (ELSA) function provides feedback to a user under stimulation, and/or to an operator monitoring stimulation, regarding the degree of muscle work associated with the current stimulation parameters, based on detected user physiological characteristics and muscle response. Sensor system 50 measures the degree of muscular response and control system 40 determines the percentage of muscular fibres that are recruited, or active, versus those that are inactive. The ELSA function thus informs the user whether he or she needs to further increase intensity of stimulation or if an increase would not be beneficial because all muscle fibres are already active, allowing the user and/or operator to measure the degree of muscle workout.

mi-Potentiation

Potentiation of a muscle is reached during a warm-up phase, which can vary according to user physiology. The muscle can be prepared for the effort to come by applying a few brief muscle contractions prior to the real exercise. This phenomenon is called potentiation. More precisely, for one action potential the twitch force is more intense once the muscle is fully potentiated. As a consequence, the maximum force can be reached more rapidly with less action potential involved. This effect can be elicited using electrosimulation and is frequently used for athletes in sports in which quick reactions and/or explosive efforts are required, for example power-lifting, sprinting, and the like. Thus, in mi-Potentiation mode, MI sensor system 50 can detect when a muscle is fully potentiated by measuring the increase in the muscle response to applied stimulation pulses.

Cramp Prevention

One common problem associated with muscle stimulation is the control of muscle cramps. It is well known that a muscle is much more likely to cramp after an effort in which the muscle has been extensively exerted. After intense efforts, electro-stimulation can be used to relax the musculature and increase blood flow in an active recovery treatment. The onset of muscle cramps during the recovery phase is painful and needs to be avoided. MI-sensor 50 and control system 40 can therefore also be used to detect the onset of muscle cramping by detecting changes in the muscle twitches due to unwanted muscle contractions.

MI-Fatigue

Figure 10:
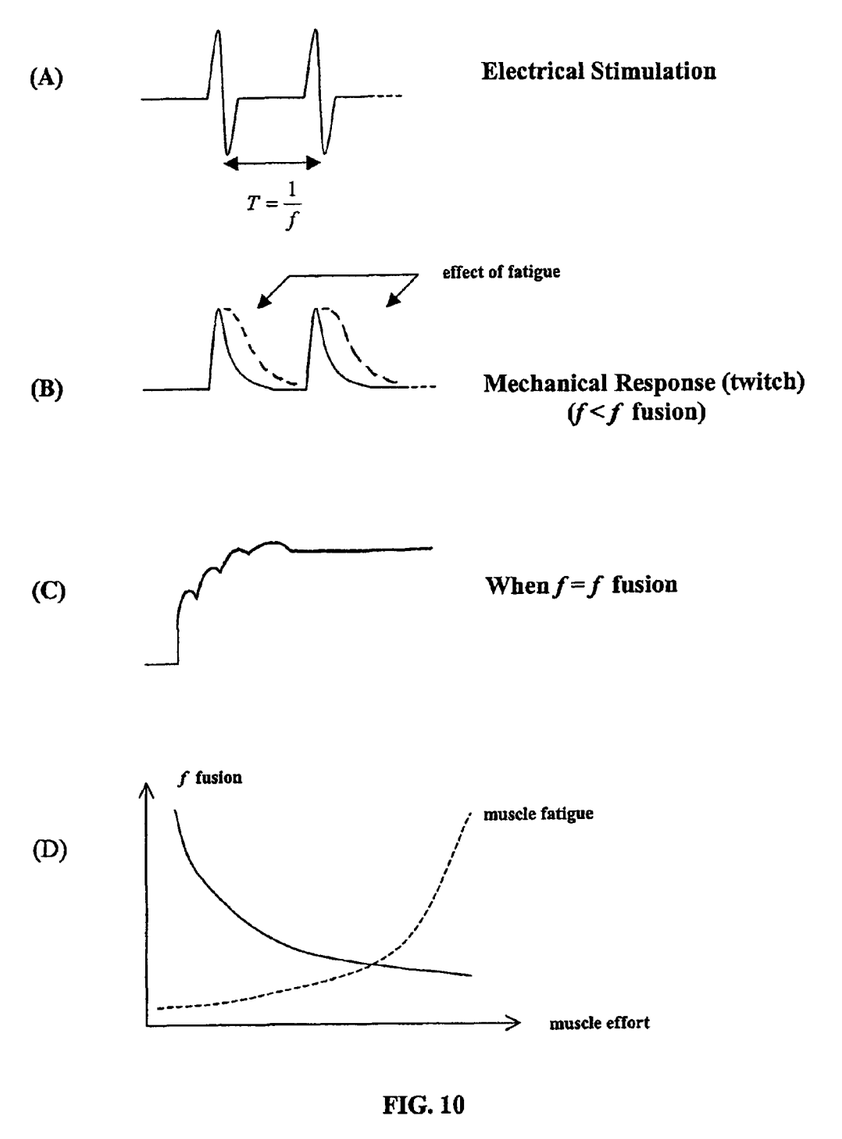
FIG. 10 depicts principles of fatigue measurement according to one embodiment of the invention.

The measurement of a degree of muscular fatigue is an indication to a user of an electro-stimulation device that there will be little or no benefit obtained from continuing muscle stimulation during a particular treatment session. In one embodiment, the detection of muscle fatigue is based upon a measurement of a shift in fusion frequency. As depicted in FIG. 10, fusion occurs when the individual mechanical responses (graph B) to the electrical excitation pulses (graph A) can no longer be differentiated in the muscle (graph C). It is known that the fusion frequency decreases when fatigue increases due to a longer relaxation time in the individual mechanical responses, shown as the dotted curve in graph B.

The system 10 of the present invention detects the fusion frequency value by measuring the reaction of the target muscle to an applied scan in excitation frequencies. In other words, the period T in graph A of FIG. 10 is progressively decreased by device 12 and control system 40 until sensor(s) 50 are unable to detect any further mechanical response in the muscle. This indicates fusion as depicted in graph C. This measurement is preferably carried out first, at the beginning of a treatment session, and can be repeated throughout the electro-stimulation program. Once the successive fusion frequencies have decreased to a certain percentage of the initial value, the user knows that his or her muscle has reached a particular level of fatigue, as illustrated in graph D of FIG. 10.

The level of muscle fatigue can thus be measured and displayed in real time by electro-stimulation system 10.

In use, one embodiment of stimulation system 10 delivers a muscle stimulation signal to a target tissue of a user as described above by electrode assembly 16. The muscle stimulation signal will typically be one of a plurality of stimulation signals delivered to the target tissue of the user as part of a muscle stimulation treatment program selected and/or customized by an operator or user. Accordingly, one embodiment of system 10 is adapted to accept a first set of input data and information from the user relating to treatment goals, status, and characteristics, and a second set of data and information from an operator. The second set can include maximum and minimum treatment program settings, available treatment programs, and other information related to a user's treatment, goals, and use of system 10. Electrode assembly 16 and sensor system 50 then detect a muscle response to the stimulation signal, wherein the response can be one or a plurality of reaction pulses.

Sensor system 50 and control system 40 automatically diagnose at least one characteristic of the target tissue from the detected muscle response. In one embodiment, the automatic diagnosis includes calculating a coefficient of correlation of a plurality of detected reaction pulses. The at least one characteristic diagnosed can be a physiological characteristic of the user, a muscle chronaxia, a fatigue level of a target muscle, or another characteristic related to muscle condition, performance, or reaction. Upon diagnosis, system 10 adjusts one or more parameters of the muscle stimulation signal and treatment program and subsequently delivers an adjusted muscle stimulation signal to a target tissue of a user.

During use, one embodiment of system 10 provides diagnostic, status, and treatment data as output. System 10 can be programmed to provide a first level of real time diagnostic and treatment data to the user and a second level of real time diagnostic and treatment data to an operator. The second level of data can include the first level of data provided to the user, in addition to more particular status, treatment, and usage data and information of interest to medical professionals, trainers, and other operators.

The adaptive muscle stimulation system and method of the invention therefore provide a compact electro-stimulation device that can operate in a plurality of modes to adapt to an individual user's physiology, target muscle group, and desired treatment mode. In particular treatment modes, the stimulation device can monitor a treatment session and provide appropriate feedback to a user based upon delivered stimulation and detected muscle feedback and response. The stimulation device can therefore be used safely and effectively by non-medical personnel for training and therapeutic applications while still providing the complete and advanced treatment modes and options required by medical professionals and certified trainers.

The invention may be embodied in other specific forms without departing from the spirit of the essential attributes thereof; therefore the illustrated embodiment should be considered in all respects as illustrative and not restrictive, reference being made to the appended claims rather than to the foregoing description to indicate the scope of the invention.

What is claimed is:

1. An automated adaptive muscle stimulation system comprising:
    an electrode assembly having an interface configured to be applied transcutaneously to a user and deliver a stimulation signal to a subcutaneous target tissue of the user;
    a sensor system that detects a muscle response; and
    a control system operably coupled to the electrode assembly and the sensor system and programmed to:
        deliver a test signal to the target tissue, wherein the test signal comprises a plurality of pulses having different pulse durations,
        receive a detected signal from the sensor system in response to the test signal, indicating at least one characteristic of the muscle response, wherein the at least one characteristic of the muscle response includes a chronaxia of the target tissue, and
        configure a stimulation signal for delivery to the target tissue based at least in part on the detected signal.

2. The muscle stimulation system of claim 1, wherein the muscle response comprises an excitability characteristic of at least one muscle.

3. The muscle stimulation system of claim 2, wherein the detected signal comprises a measurement of the chronaxia.

4. The muscle stimulation system of claim 3, wherein the control system automatically initiates the test signal.

5. The muscle stimulation system of claim 4, wherein the test signal includes at least one pulse.

6. The muscle stimulation system of claim 5, wherein the stimulation signal comprises at least one different parameter than the test signal.

7. The muscle stimulation system of claim 6, wherein at least one parameter of the stimulation signal is automatically configured in response to the detected signal.

8. The muscle stimulation system of claim 7, wherein at least one parameter of the stimulation signal is set at a pulse width based on the measured chronaxia of the target tissue.

9. The muscle stimulation system of claim 8, wherein the pulse width approximates the chronaxia of the target tissue.

10. The muscle stimulation system of claim 1, wherein the sensor system includes an accelerometer.

11. The muscle stimulation system of claim 10, wherein the accelerometer is configured to detect the presence of a muscle response.

12. A method of providing muscle stimulation, the method comprising the steps of:
    delivering a test signal through a user's skin to a subcutaneous target tissue of the user, wherein delivering the test signal comprises applying at least one of a plurality of pulses having different pulse durations;
    detecting at least one muscle response;
    automatically determining a muscle characteristic from the at least one detected muscle response, wherein the muscle characterstic includes a chronaxia; and
    applying a stimulation signal to the target tissue in response to the muscle characteristic.

13. The method of claim 12, further comprising adjusting at least one parameter of the stimulation signal based at least in part on the muscle characteristic.

14. The method of claim 13, wherein the test signal is delivered prior to beginning a stimulation program.

15. The method of claim 14, comprising adjusting at least one parameter of the stimulation signal based on the test signal.

16. The method of claim 15, wherein the adjusting of the at least one parameter of the stimulation signal is done automatically.

17. The method of claim 16, wherein adjusting of the at least one parameter of the stimulation signal is done prior to applying the stimulation signal.

18. The method of claim 16, wherein adjusting at least one parameter of the stimulation signal includes setting a pulse width to approximate the chronaxia of the target tissue.

19. The method of claim 18, comprising determining the value of chronaxia at least in part by mathematical curve fitting.

20. The method of claim 12, wherein detecting the presence of a muscle response comprises detecting with an accelerometer.

* * * * *